United States Patent
Coste et al.

(10) Patent No.: US 6,315,554 B1
(45) Date of Patent: Nov. 13, 2001

(54) DENTAL RESTORATIVE SHADE GUIDE AND METHOD OF SELECTING A DENTAL RESTORATIVE SHADE

(75) Inventors: Andrew J. Coste, Swarthmore, PA (US); Junjie Sang; Xiuling Wang, both of Magnolia, DE (US); Lisa Durst, Dewey Beach, DE (US)

(73) Assignee: Dentsply Research & Development Corp.

( * ) Notice: Subject to any disclaimer, the term of this patent is extended or adjusted under 35 U.S.C. 154(b) by 0 days.

(21) Appl. No.: 09/712,446

(22) Filed: Nov. 14, 2000

Related U.S. Application Data

(60) Provisional application No. 60/166,014, filed on Nov. 17, 1999.

(51) Int. Cl.[7] .................................................. A61C 19/10
(52) U.S. Cl. ............................................................ 433/26
(58) Field of Search ..................................... 433/26, 203.1

(56) References Cited

U.S. PATENT DOCUMENTS

| | | | |
|---|---|---|---|
| 4,382,784 | 5/1983 | Freller | 433/26 |
| 4,608,015 | 8/1986 | Smigel | 433/26 |
| 4,618,325 | 10/1986 | Appelle | 433/26 |
| 4,810,193 | 3/1989 | Wieder | 433/26 |
| 4,828,117 | 5/1989 | Panzera | 206/63.5 |
| 4,919,617 | 4/1990 | Antons et al. | 433/26 |
| 4,978,296 | 12/1990 | Antons et al. | 433/26 |
| 5,055,040 | 10/1991 | Clar | 433/26 |
| 5,066,227 | 11/1991 | Pozzi | 433/26 |
| 5,078,598 | 1/1992 | Neisse | 433/26 |
| 5,114,340 | 5/1992 | Hahn | 433/26 |
| 5,149,267 | 9/1992 | Longhini et al. | 433/26 |
| 5,240,414 | 8/1993 | Thompson | 433/26 |
| 5,257,931 | 11/1993 | Pozzi | 433/26 |
| 5,261,815 | 11/1993 | Pozzi | 433/26 |
| 5,482,459 | 1/1996 | Yarovesky et al. | 433/26 |
| 5,498,157 | 3/1996 | Hall | 433/26 |

FOREIGN PATENT DOCUMENTS

| | | |
|---|---|---|
| 0 591 958 | 6/1998 | (EP) . |
| 96/06577 | 3/1996 | (WO) . |
| 96/06578 | 3/1996 | (WO) . |

*Primary Examiner*—Cary E. O'Connor
(74) *Attorney, Agent, or Firm*—Douglas J. Hura; James B. Bieber

(57) ABSTRACT

A shade guide (10) has a base (11) and a plurality of indicia tabs (15) carried by stems (14). Base (11) also includes a shade calculation table (20) containing at least the necessary recipe components of a foundation, body and enamel layers (22, 23 and 24) to achieve the shade of a given tab (15).

6 Claims, 4 Drawing Sheets

DENTAL RESTORATIVE SHADE GUIDE AND METHOD OF SELECTING A DENTAL RESTORATIVE SHADE

This application claims the benefit of provisional application No. 60/166,014, filed Nov. 17, 1999.

TECHNICAL FIELD

The present invention is a shade guide for selecting a tooth restoration esthetic and for providing a recipe to achieve the selected esthetic. More particularly, the invention relates to a shade guide having a plurality of tooth specimens having different shade characteristics, and a shade recipe reference for each shade characteristic. Specifically, the shade recipe reference provides a coded foundation layer (opacious dentin), a body layer (regular dentin) and an enamel layer (translucent layer), which together produce the selected shade characteristic. The invention also relates to a method of selecting a shade characteristic.

BACKGROUND OF THE INVENTION

Dental restoratives are well known in the art. The term "restorative" encompasses for example, bridges, inlays, onlays, veneers, filling materials, composite materials, entire artificial teeth and the like. When a tooth is damaged, it is desirable not only to restore the tooth to a useful state by using the appropriate restorative and restorative technique, but also to match the restored tooth to approximate the original tooth's color or shade characteristics. This is primarily for esthetic concerns.

Because of the desire to match the original tooth shade characteristics, or those of the surrounding teeth, it has been common practice to provide materials that will change the shade of the restorative to match the desired quality. It has also been a common practice to use a shade guide having a number of tabs, teeth or other indicia showing a given color. Once the shade has been chosen, the shade guide references a mix of materials to achieve the desired shade. The dental practitioner then prepares the restorative with the given shade and applies it according to the conventional technique.

It has been found however, that natural teeth are not simply one shade of material. The tooth tends to have varying shades, translucency and opacity throughout its structure. Therefore, the previous methods of restoring a tooth have proven to be deficient with respect to shade characteristics. Further, no shade guide has heretofore existed which can be employed to more accurately match the varying shade characteristics of natural teeth.

A need exists therefore, for a shade matching system that will more closely approximate the varying shade characteristics of natural teeth. A need also exists for an efficient means of selecting a shade that is more true to the shade qualities of natural teeth.

DISCLOSURE OF THE INVENTION

It is therefore, an object of the present invention to provide a shade guide.

It is another object of the invention to provide such a shade guide that can be used to select a shade characteristic.

It is a further object of the invention to provide such a shade guide wherein the recipe for a given restorative is contained on the shade guide itself.

It is yet another object of the invention to provide such a shade guide which contains a recipe taking into account at least the foundation (opacious) layer quality, the body (regular dentin) layer quality and the enamel (translucent) layer quality so as to achieve a selected restorative shade.

These and other objects of the invention, together with the advantages thereof, will be apparent to those skilled in the art by reference to the following description and the attached drawings.

PREFERRED EMBODIMENTS FOR CARRYING OUT THE INVENTION

Figure 1:
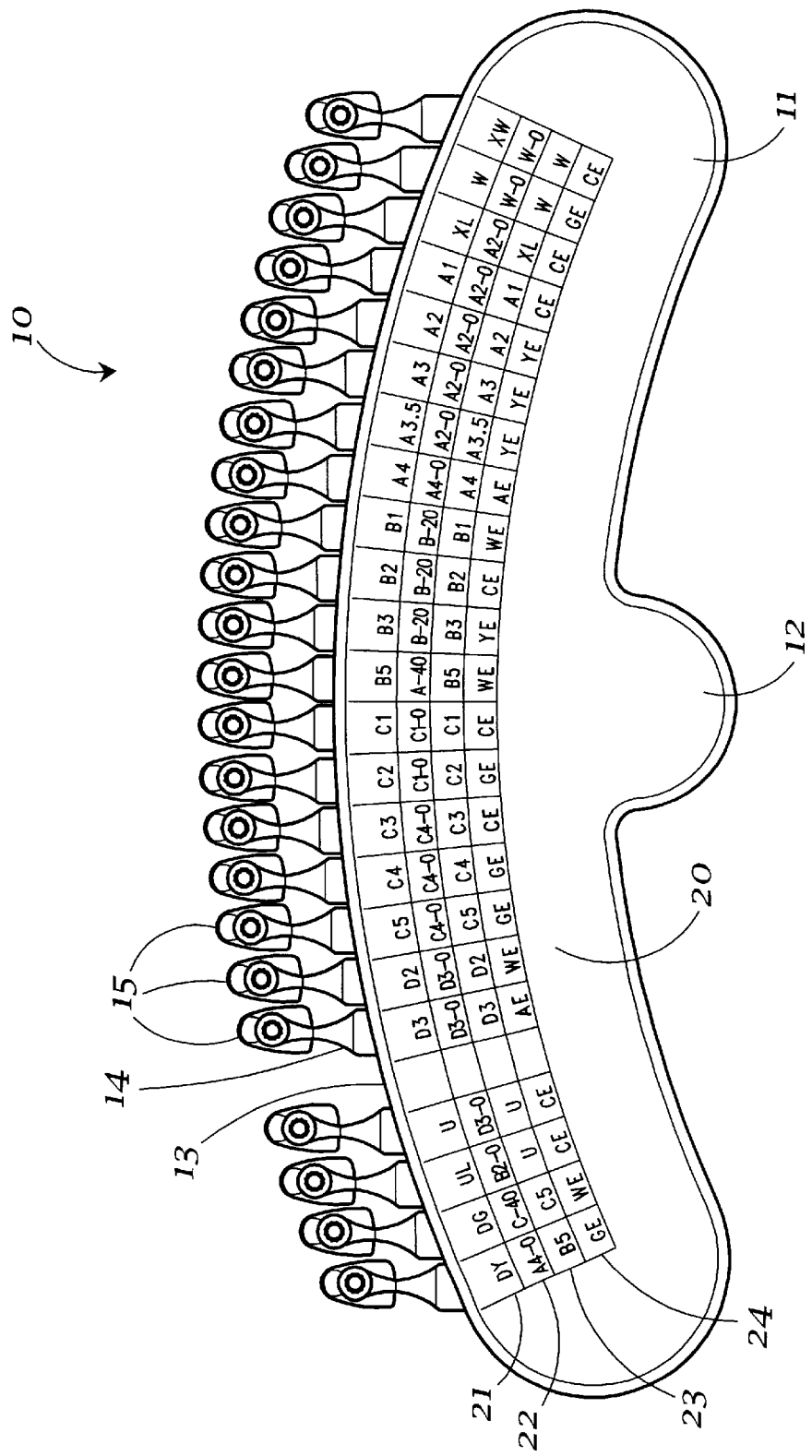
FIG. 1 is a top plan view of a shade guide embodying the concepts of the present invention.

A shade guide embodying the concepts of the present invention as shown by way of example on the drawings by numeral 10. Shade guide 10 includes a base 11 and may include a finger or indicia tab 12. Base 11 is provided with means, such as plurality of slots 13 for holding a plurality of stems 14. Stems 14 carry at their opposite ends a tooth indicia or tab 15. Tabs 15 may be in any form showing a shade of a tooth restorative, and preferably are in the shape of a tooth as is depicted on the drawings. More preferably, each tab 15 is of a different shade from other tabs 15 of shade guide 10. Base 11 also carries on at least one side thereof, a shade calculation table 20. Shade calculation table 20 shows the formulation necessary to achieve the shade of a given tab 15. Further, shade calculation table 20 also carries a shade indicator reference 21 for each tab 15. It will be understood that shade indicator reference 21 for a given shade of a tab 15 is an arbitrary designation, and need not be the shade indicator reference as depicted on the drawings.

While the present invention has application to any type of restorative or restorative technique, it has particular application to composite restorative materials such as those marketed by DENTSPLY International Inc. of York, Pa. An exemplary composite material is for example, DENTSPLY's Esthet-X™ material.

Shade calculation table 20 also carries a recipe showing at least the foundation layer (opacious dentin), a body (regular or dentin) layer and an enamel (translucent) layer necessary to achieve the shade of a given tab 15. The preferred means for accomplishing this is shown in shade calculation table 20. That is, a plurality of rows and columns are provided containing the necessary information. Shade indicator references 21 are shown as being a row immediately adjacent or proximate to the plurality of tabs 15, such that a given shade indicator reference 21 is physically adjacent the tab 15 or its stem 14. The foundation or opacious dentin layer is shown in row 22, the body layer is shown as row 23 and the enamel layer is shown as row 24. It would be appreciated that the tooth shade indicator reference 21, the foundation layer reference 22, the body layer 23 and the enamel layer 24 necessary to achieve or prepare the shade of a given tab 15 form a single column.

Therefore, in use, the dental practitioner selects a shade as embodied in a given tab 15. To prepare the restorative to match that shade, it is merely necessary to select the components of the foundation, body and enamel layers 22, 23, and 24 respectively, in the column immediately below the tab 15. In this way, the dental practitioner is insured of preparing the specific restorative the same way each time. Hence, a proper shade match can be achieved.

Figure 2:
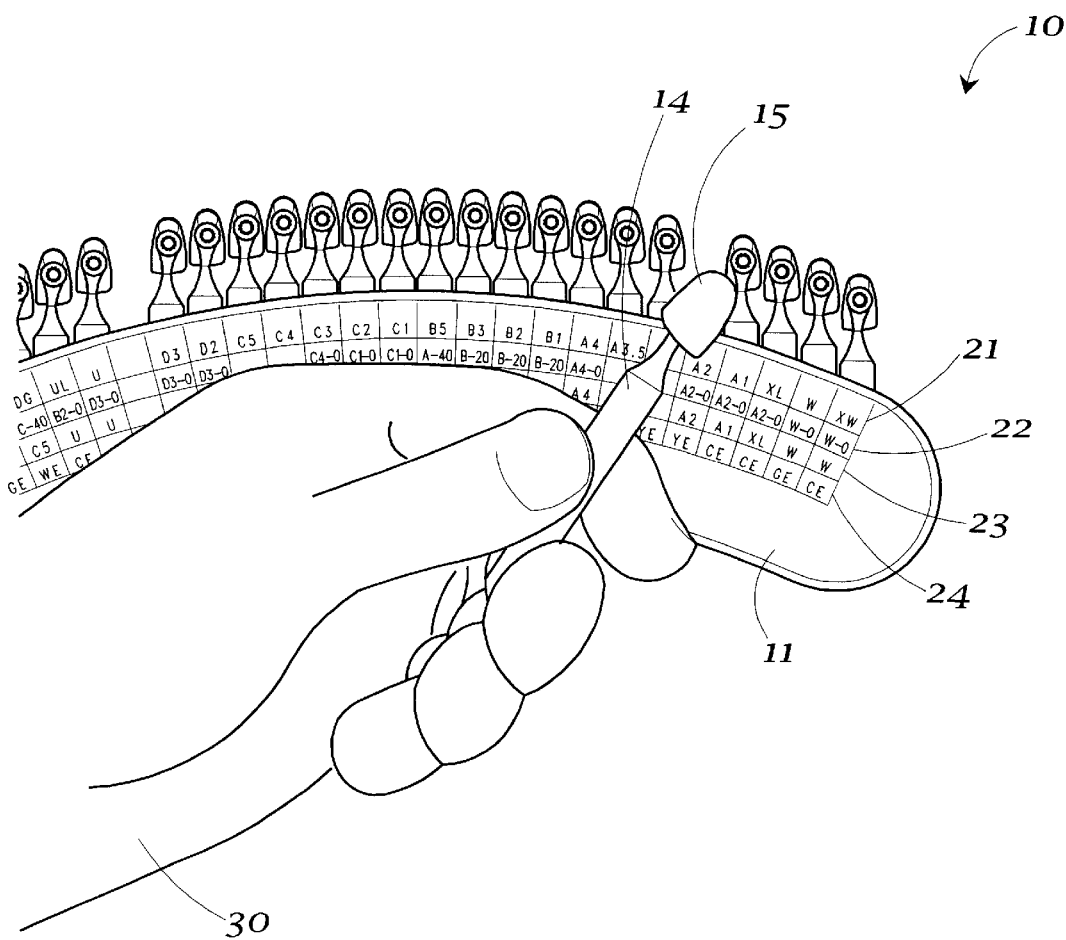
FIG. 2 is top plan view of a portion of the shade guide of FIG. 1 showing a user having removed one of the shade tabs.
Figure 3:
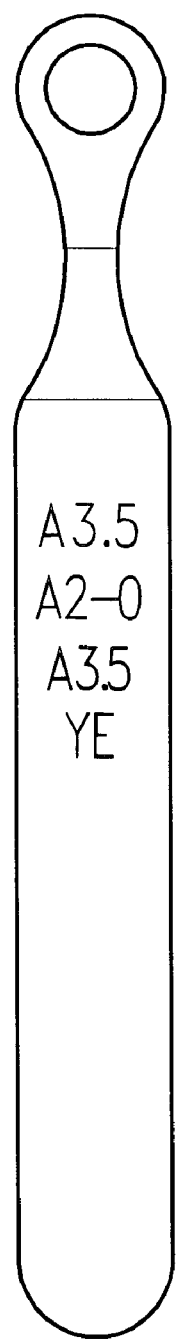
FIG. 3 is a schematic representation of a shade indicator tab carrying a shade recipe.

As shown in FIG. 2, a user 30 may remove an individual tab 15 by removing its stem 14 from slot 13 of base 11. The tab 15 can be brought into close proximity with the oral cavity (not shown) in order to visually match the given tab 15 to the tooth to be restored and/or the adjacent teeth. It is also within the scope of the invention, as shown in FIG. 3, which is a schematic representation of a stem 14, that the shade indicator reference, foundation layer, body layer and enamel layer can be carried by the stem 14 itself.

Figure 4:
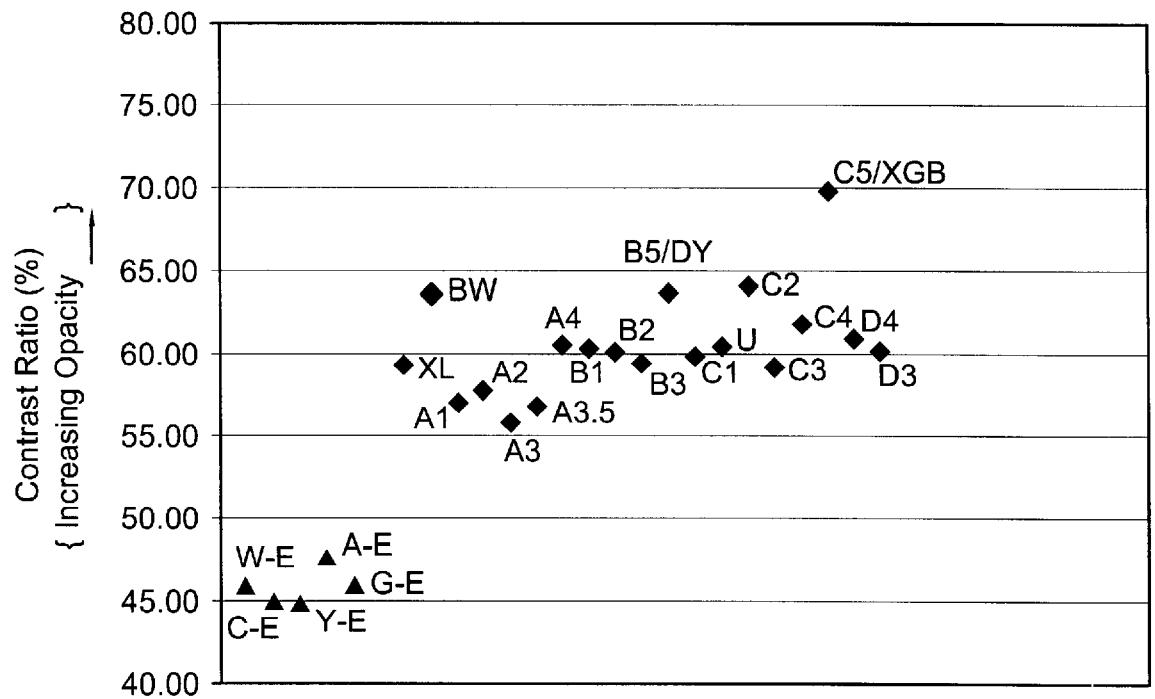
FIG. 4 is a graphic representation of the Contrast Ratio of the recipe components shown on the shade guide of FIG. 1.

It is to be appreciated that any restorative material is within the scope of the present invention, as long as it takes into account at least a foundation, body and enamel layer as discussed hereinabove. For example, a restorative material having the contrast ratios necessary to achieve varying shades is shown by way of example in FIG. 4. FIG. 4 is a graphic representation of the contrast ratios of the foundation (represented by squares), body (diamonds) and enamel (triangle) references shown in shade calculation table 20. It will be appreciated that other layers beyond the three exemplified herein are within the scope of the invention.

Table 1 shows the shade indicator reference and the shade recipe of shade guide 10.

TABLE I

"SHADE RECIPE"

| SHADE INDICATOR REFERENCE | SHADE RECIPE |
|---|---|
| XW | W-O, W, CE |
| W | W-O, W, GE |
| XL | A2-O, XL, CE |
| A1 | A2-O, A1, CE |
| A2 | A2-O, A2, YE |
| A3 | A2-O, A3, YE |
| A3.5 | A2-O, A3.5, YE |
| A4 | A4-O, A4, AE |
| B1 | B2-O, B1, WE |
| B2 | B2-O, B2, CE |
| B3 | B2-O, B3, YE |
| B5 | A4-O, B5, WE |
| C1 | C1-O, C1, CE |
| C2 | C1-O, C2, CE |
| C3 | C4-O, C3, CE |
| C4 | C4-O, C4, GE |
| C5 | C4-O, C5, GE |
| D2 | D3-O, D2, WE |
| D3 | D3-O, D3, AE |
| U | D3-O, U, CE |
| UL | B2-O, U, CE |
| DG | C4-O, C5, WE |
| DY | A4-O, B5, GE |

Use of the shade guide 10 according to the present invention enables dental clinicians to achieve natural "tooth-like" restorations, beyond that heretofore achieved in the art. In order to facilitate this, shade guide 10 provides for restoration of a tooth from the inside out. That is, each shade tab 15 of shade guide 10 is constructed by blending three different shaded layers, representing the opacious, regular (dentin) body, and translucent enamel portions.

To use the shade guide 10, the dental clinician selects the appropriate tab to predict the desired final restoration aesthetic. Once selected, the shade tab handle or stem 14 and/or the shade guide 10 outline the "recipe" used to create the particular shade tooth. By selecting the corresponding shades, according to the shade calculation table 20, and layering the shades sequentially into the prepared tooth preparation, the dental clinician can achieve the desired result exactly portrayed by tab 15. For example, to create a final restoration of the designation "A3", a foundation layer of A2-0 (opacious dentin) is placed followed by A3 body (regular [dentin] body) and finally covered with YE (translucent enamel). These designations are contained in the column below tab 15 carrying the reference 21 of A3.

Both the color or shade and the translucency (contrast ratio) determine the esthetic quality of a composite restorative. Color is important because the shade match between the restoration and its surrounding teeth should be substantially indistinguishable. Translucency of a restorative will provide the added "life-like" vitality and natural appearance of the completed restoration. Translucency may be measured as contrast ratio, wherein a material becomes less translucent (more opaque) as the contrast ratio increases. The translucency range as depicted by the composite restoratives exemplified in FIG. 4 has been developed to match that of human enamel and dentin. The translucency (contrast ratio) of the restoratives spans from ca. 40% in Translucent Enamel Shades to ca. 80% in Opaceous Dentin Shades (FIG. 4).

Custom blending of the three different opacities allows the dental clinician to create restorations possessing natural esthetic beauty. The customized translucency gradient of the restorative as exemplified in FIG. 4 creates superior matching effects. That is, the restoration acquires the appearance of its surroundings, making it substantially invisible within the tooth and the adjacent arch. The combination (overlayering) of the selected Opaceous Dentin/Regular Body/Translucent Enamel shades with the customized translucency gradient makes the composite as exemplified in FIG. 4 and as employed according to shade guide 10, a complete restorative system.

It should be evident therefore, that a shade guide as described is useful in accomplishing the objects as set forth hereinabove. Further, the use of the shade guide is also an improvement over the shade guides heretofor known in the art. While the shade guide as described and shown in the drawings is useful with the restorative formulation as also described, it would be appreciated that the shade guide has applications to other restorative materials and/or restorative techniques.

What is claimed is:

1. A dental shade guide for use in preparing a dental restoration, comprising a base supporting both a plurality of indicia tabs and a shade calculation table, wherein each said indicia tab indicates a tooth shade, and wherein said shade calculation table provides a formula for preparing a tooth restoration corresponding to at least one of said indicated shades, and also wherein said formula includes the specification of at least a foundation layer, a body layer and an enamel layer.

2. A shade guide as in claim 1, wherein said indicia tab is shaped like a human tooth.

3. A shade guide as in claim 1, wherein said base supports a plurality of stems, each said stem carrying at least one of said indicia tabs.

4. A method of preparing a dental restorative comprising the steps of:

matching the shade of the restorative to the natural tooth shade or the natural shade of surrounding teeth, by using a dental shade guide comprising a base supporting both a plurality of indicia tabs and a shade calculation table, wherein each said indicia tab indicates a tooth shade, and wherein said shade calculation table provides a formula for preparing a tooth restoration corresponding to at least one of said indicated shades, and also wherein said formula includes the specification of at least a foundation layer, a body layer and an enamel layer; preparing a dental restorative according to said formula.

5. A dental restorative prepared according to the method of claim 4.

6. A method of assisting in the preparation of a dental restorative comprising the step of providing a dental shade guide comprising a base supporting both a plurality of indicia tabs and a shade calculation table, wherein each said indicia tab indicates a tooth shade, and wherein said shade calculation table provides a formula for preparing a tooth restoration corresponding to at least one of said indicated shades, and also wherein said formula includes the specification of at least a foundation layer, a body layer and an enamel layer.

* * * * *